United States Patent [19]

Lindmayer et al.

[11] 4,342,310

[45] Aug. 3, 1982

[54] HYDRO-PNEUMATIC JET INJECTOR

[76] Inventors: Istvan Lindmayer, 4390 Gilles St., Pierrefonds, Prov. of Quebec, Canada, H9H 2N4; Karim Menassa, 3035 Noorduyn, St. Laurent, Prov. of Quebec, Canada, H4R 1A1

[21] Appl. No.: 167,395

[22] Filed: Jul. 8, 1980

[51] Int. Cl.³ .............................................. A61M 5/30
[52] U.S. Cl. ................................ 128/207.25; 222/389; 222/334
[58] Field of Search ....................... 128/207.25, 207.23, 128/218 A, 218 G, 234, 235, 273, 218 C, 218 R; 222/334, 389, 386.5, 339, 391

[56] References Cited

U.S. PATENT DOCUMENTS

| 963,051 | 7/1910 | Kooken | 128/234 |
|---|---|---|---|
| 2,316,095 | 4/1943 | Mead, Jr. | 128/218 R |
| 2,317,299 | 4/1943 | Peters | 222/391 |
| 2,635,601 | 4/1953 | May | 128/207.25 |
| 2,764,977 | 10/1956 | Ferguson | 128/207.25 |
| 2,821,193 | 1/1958 | Ziherl et at. | 128/207.23 |
| 3,255,936 | 6/1966 | Healy et al. | 222/389 |
| 3,425,413 | 2/1969 | Stephens | 128/207.25 |
| 3,526,225 | 9/1970 | Isobe | 128/218 C |
| 3,805,783 | 4/1974 | Ismach | 128/207.23 |
| 3,977,574 | 8/1976 | Thomas | 128/218 R |

FOREIGN PATENT DOCUMENTS 173244  9/1979  Hungary .

*Primary Examiner*—Henry J. Recla
*Attorney, Agent, or Firm*—George A. Seaby

[57] ABSTRACT

A pneumatic jet injector for needleless injection of a liquid medicine into the skin includes a pistol-shaped casing including a barrel, a handle and a trigger; a compression chamber in one end of the casing for a gas which is partially liquefied under pressure; a first piston movable in the casing against the gas; a charging liquid in the handle which is pumped against the first piston using the trigger and a second piston in the handle; a piston rod movable in the barrel with the first piston for creating a partial vacuum in the barrel for drawing medicine into the barrel through an inlet containing a one-way valve; a discharge orifice in one end of the barrel for discharging medicine into the skin of a user; and a safety catch in the handle for locking the first and second pistons in the loaded or charged position, and for releasing the pistons whereby at least a portion of the liquid in the compression chamber becomes gaseous moving the piston rod against the medicine to discharge the medicine through the orifice into the skin, while the charging liquid returns to the handle.

9 Claims, 6 Drawing Figures

4,342,310

HYDRO-PNEUMATIC JET INJECTOR

BACKGROUND OF THE INVENTION

1. Field of the Invention

This invention relates to an injection device and in particular to a hydro-pneumatic jet injector for administering medicine through the skin of humans or animals without the use of skin-piercing needles.

2. Discussion of the Prior Art

Jet injection devices of the type disclosed herein have met limited acceptance because of the high pressures required to perforate the skin of humans or animals. Such high pressure has been achieved thus far by various means, including explosives, hydraulic pumps, carbon dioxide cylinders and springs. However, several problems have been encountered with jet injectors.

Instruments using explosive materials are definitely dangerous and their use is not recommended. Hydraulic devices require heavy equipment, such as pumps, high pressure tubing and hydraulic controls, which are not only cumbersome but also expensive. Small carbon dioxide cylinders are well suited for portable instruments, but it is very difficult with such instruments to obtain the constant pressure needed to control the dose of medicine to be injected. It will be appreciated that control of the dose of medicine is most important. Moreover, such a device requires storing of an adequate supply of carbon dioxide cylinders. Other pneumatic instruments employ gas bottles or gas reservoirs and high pressure tubing. Such equipment is, however, bulky and not portable.

The most commonly used instruments are operated by steel springs. However, for the usual doses of 1.0 ml springs having long strokes are needed, due to the inherent characteristic of compressed springs to lose their strength as they expand. Thus, long and heavy springs are required to provide the high pressure required to push the injection fluid through the skin. In order to load the springs, it is necessary to use hydraulic cylinders and associated equipment, which is bulky and expensive.

The object of the present invention is to at least partially alleviate the problems described hereinbefore by providing a jet injector which is portable, and which does not require any cumbersome auxiliary equipment

GENERAL DESCRIPTION OF THE INVENTION

Accordingly, the present invention relates to a jet injector for administering a fluid medicine through the skin comprising:

(a) an elongated tubular casing;

(b) handle means substantially perpendicular to said casing;

(c) plug means in said casing, said plug means dividing the interior of said casing into a medicine chamber and a compression chamber, said compression chamber containing a substance which is gaseous at normal room temperature and which converts to a liquid when subjected to pressure;

(d) an inlet duct in said casing for introducing medicine into said medicine chamber;

(e) a discharge orifice in said casing for discharging medicine from said medicine chamber into the skin;

(f) first piston means slidably mounted in said compression chamber for movement from a rest position toward said substance to a charged position and away from said substance to the rest position;

(g) rod means connected to said first piston means slidable in said plug means and extending into said medicine chamber for drawing medicine into and discharging medicine from said medicine chamber;

(h) a charging chamber in said handle means containing a liquid;

(i) a pressure chamber between said plug means and said piston means for receiving liquid from said charging chamber for pressing the first piston means against the substance;

(j) second piston means in said handle means;

(k) trigger means connected to said casing for moving said second piston means against said charging liquid whereby said charging liquid is caused to pass from said charging chamber into said pressure chamber to move said first piston against the substance to the charged position to liquify a portion of said substance, and to cause said rod to move partially out of said medicine chamber for drawing medicine into the medicine chamber;

(1) safety catch means in said handle means for locking said first and second piston means in the charged position, and for releasing said first and second piston means to cause said rod means to force said medicine through said discharge orifice while the charging liquid is returned to the charging chamber.

BRIEF DESCRIPTION OF DRAWINGS

A preferred embodiment of the invention will now be described with reference to the accompanying drawings, wherein.

DESCRIPTION OF PREFERRED EMBODIMENT STRUCTURE

Figure 1:
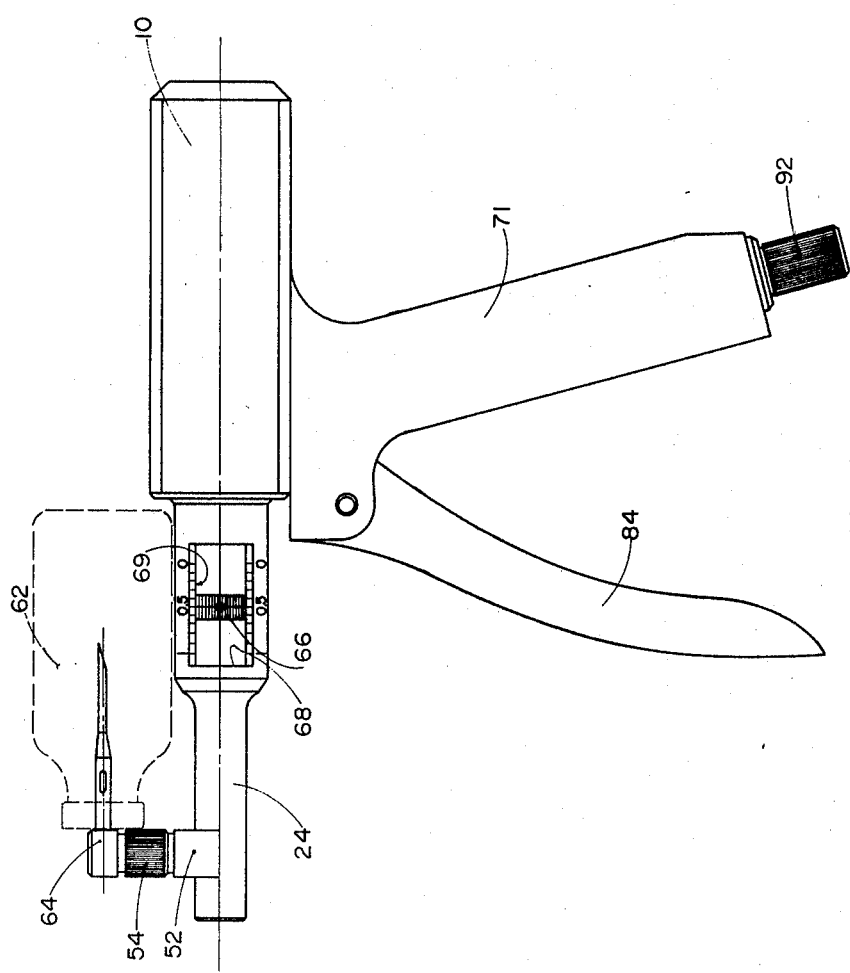
FIG. 1 is a side elevation of the hydro-pneumatic injector in accordance with a preferred embodiment of the invention.
Figures 2, 2A:
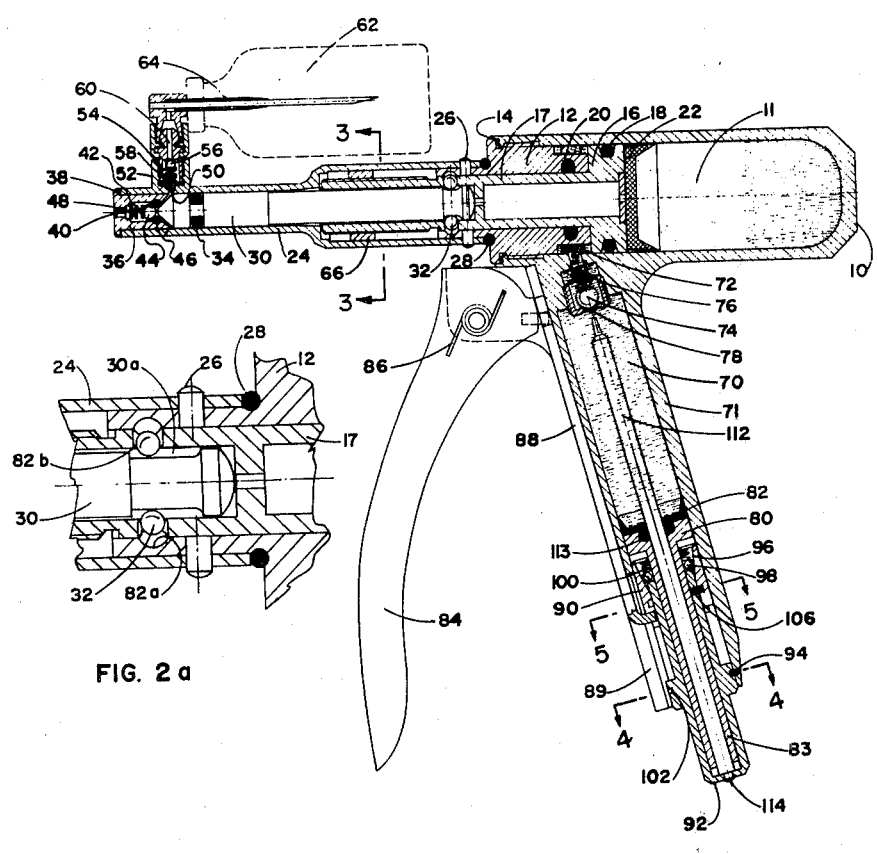
FIG. 2 is a longitudinal sectional view of the jet injector of FIG. 1.
FIG. 2a is a longitudinal sectional view of the middle of the injector of FIGS. 1 and 2 on a larger scale.

With reference to FIGS. 1 and 2, the jet injector of the present invention includes an elongated tubular casing 10, with a handle 71 and a trigger 84 substantially perpendicular thereto. A plug 12 (FIG. 2) connects the rear end of the casing 10 to a front tubular barrel 24. The rear end of the casing defines a compression chamber 11, which contains a substance such as chlorotrifluoromethane which has a critical temperature above normal room temperature. The substance in the compression chamber 11 changes to a liquid when subjected to pressure at normal room temperatures, and changes back to a gas when the pressure is released. There is sufficient of the substance in the chamber 11 that some liquid is always present in such chamber.

The plug 12 is threaded externally for coupling with the internally threaded front end of the rear handle end of the casing 10. A gasket 14 provides a fluid-tight seal between the plug 12 and the handle portion of the casing. The plug 12 is connected to the barrel 24 by pins 26.

A seal 28 defined by an O-ring 28 is provided between the plug and barrel. A piston 16 is slidably mounted in the compression chamber 11 for longitudinal reciprocating movement between a rest position (FIG. 2) and a charged position (not shown) in which the piston compresses the gas to convert at least a portion of the gas into a liquid. An O-ring 18 seals the piston 16 with respect to the interior of the handle end of the casing 10.

A hollow piston rod 17 integral with the piston 16 extends forwardly from the piston and is slidable in the plug 12. The piston rod 17 is sealed with respect to the plug 12 by an O-ring 20. A gasket 22 on the rear, compression chamber end of the piston 16 seals the chamber 11 from the remainder of the casing 10.

A second piston rod 30 is slidably mounted in the barrel 24. The rear or handle end of the piston rod 30 is releasably connected to the piston rod 17 of the piston 16 by balls 32. The balls 32 are loosely retained in holes in the rod 17, and extend radially into an annular groove 30a in the piston rod 30. When the piston rod 30 is moved forward a sufficient distance in the barrel 24, the balls 32 are pushed outwardly into an annular groove 82a (FIG. 2a) in the plug 12, releasing the piston rod 30 and locking the rod 17 in the forward position. The sides of the groove 82a are bevelled, i.e. include lips 82b, which prevent the balls 32 from falling into the piston rod 17 when the piston rod 30 is removed. An O-ring 34 seals the front end of the piston rod 30 with respect to the barrel 24.

A plug 36 closes the front end of the barrel 24, with a gasket 38 between the plug and barrel. A small orifice 40 is provided in the otherwise closed front end of the plug 36 communicating with hollow interior 42 of the plug. A one-way check valve defined by a ball 44 is slidably mounted in the plug 36. The ball 44 is normally held against an O-ring 46 in the rear end of the plug 36 by a helical spring 48.

An inlet orifice 50 for injectable fluid is provided in the barrel 24 near the front end thereof. An inlet duct defined by an internally threaded sleeve extends outwardly from the barrel 24 around the orifice 50 for receiving the externally threaded end of a hollow connector 54. The connector 54 contains a one-way valve defined by a ball 56 and a helical spring 58 for biasing the ball 56 against a valve seat in central passage 60 of the connector. A container 62 of injection fluid is mounted on the connector 54 by inserting a needle assembly 64 into the container 62, and connecting the externally threaded outer end of the needle assembly to the internally threaded rotatable coupling on the outer end of the connector 54. The container could also be mounted on the casing 10 and connected to the connector 54 by tubing (not shown).

Figure 3:
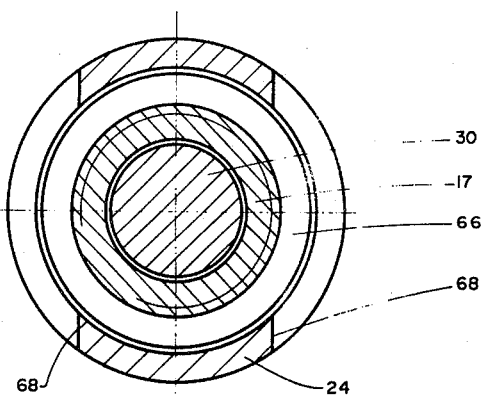
FIG. 3 is a cross-section taken generally along line 3—3 of FIG. 2.
Figure 5:
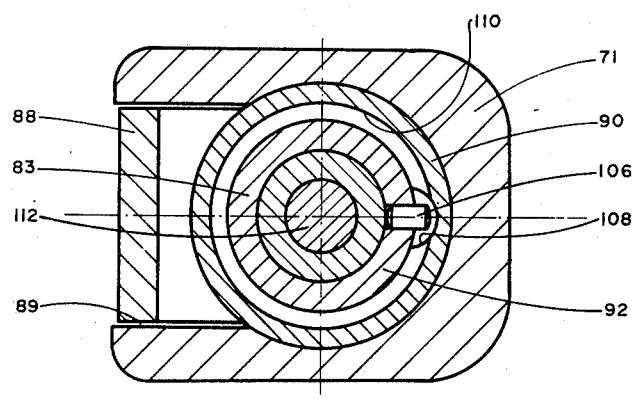
FIG. 5 is a cross-section taken generally along line 5—5 of FIG. 2.

As shown in FIGS. 1 and 3 of the drawings, an adjustable ring 66 is threaded onto the piston rod 17 of the piston 16 for determining the stroke of the piston 16, i.e. the distance the piston 16 moves into the compression chamber 11 from the rest to the charged position. At the rear end of the stroke of the piston 16, the ring 66 butts against the forward end of the plug 12. Openings 68 are provided in the sides of the barrel 24 permitting adjustment of the position of the ring 66. Calibration markings 69 (FIG. 1) on the side of the barrel 24 indicate the dosage, which is determined by the ring 66 position.

The handle or grip 71 contains a charging chamber 70 for a liquid such as oil. The chamber 70 can be connected to a pressure chamber 72 between the front of the piston 16 and a shoulder on the plug 12. When the piston 16 moves into the chamber 11, the pressure chamber 72 enlarges to receive liquid from the charging chamber 70. Liquid from the chamber 70 passes through a valve defined by a ball 74 and a helical spring 76, which biases the ball against a seat 78. A piston 80 is slidably mounted in the chamber 70, with a gasket 82 on the upper end of the piston sealing the piston 80 from the liquid in the chamber 70. A hollow piston rod 83 extends downwardly from the piston 80.

The piston 80 and rod 83 are moved by operation of the trigger 84, which is pivotally connected to the casing 10. The trigger 84 is biased away from the handle 71 by a spring 86. The trigger 84 is connected to a bar 88, which is slidably mounted in a slot 89 in the front side of the handle 71. The bottom end of the bar 88 is connected to a sleeve 90, which is slidably mounted on a tubular safety catch 92. The catch 92 is slidable on the piston rod 83. In the safety position (FIG. 2), the catch 92 is locked to the handle 71 by a pin 94. The sleeve 90 includes a frusto-conical interior surface 96, which defines a cavity with the top end of the catch 92 for balls 98. The balls 98 are biased downwardly into the cavity by a helical spring 100. When the sleeve 90 is caused to move upwardly by operation of the trigger 84, the balls 98 are jammed between the surface 96 of the sleeve 90 and the piston rod 83 to force the piston 80 upwardly. When the trigger 84 is released, the sleeve 90 is moved downwardly by the spring 86. The balls 98 are released, and are moved downwardly by the spring 100. Pumping of the trigger 84 is continued to cause stepwise movement of the piston 80, and consequently the pumping of liquid from the charging chamber 70 into the pressure chamber. Thus, the gas in the compression chamber 11 is compressed, changing into a liquid.

Figure 4:
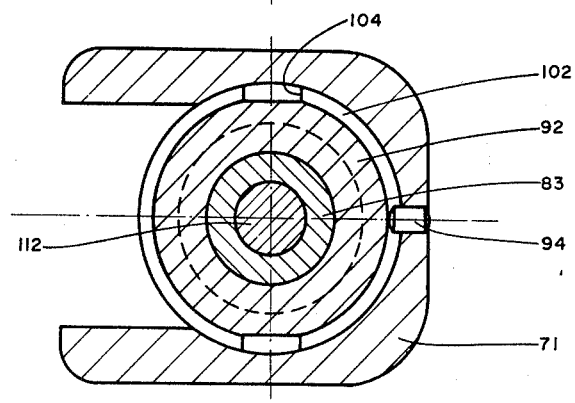
FIG. 4 is a cross-section taken generally along line 4—4 of FIG. 2.

Referring now to FIGS. 2 and 4, the pin 94 extends into a circumferential slot 102 in the catch 92. The catch 92 can be rotated 90° so that the pin 94 enters a longitudinally extending slot 104 in the catch. A pin 106 normally extends from the catch 92 into a longitudinally extending slot 108 in the sleeve 90. Movement of the pin 94 into the slot 104 results in movement of the pin 106 from the slot 108 into a circumferential slot 110 in the sleeve 90. Thus, rotation of the safety catch through 90° releases the lock from the handle 71 and causes direct engagement between the catch 92 and the sleeve 90.

A rod 112 is connected to the safety catch 92 by a screw 114. The rod 112 extends upwardly through the piston 80 and the chamber 70. On O-ring 113 provides a fluid seal between the rod 112, piston 80 and the chamber 70. When the safety catch 92 is rotated 90° from the locked position, movement of the trigger 84 moves the safety catch 92 and the rod 112 upwardly to engage the ball 74 to open the valve. Liquid in the pressure chamber can then return to the charging chamber 70. Thus, the compressed gas and liquid in the compression chamber 11 are free to expand, driving the piston 16 and the rods 17 and 30 forwardly to push the injection fluid out of the orifice 40 and into the skin under the constant pressure of the expanding gas.

OPERATION

With the safety lock 92 in the safety position, the trigger 84 is pumped until sufficient charging fluid from the chamber 70 has been forced into the pressure chamber to move the piston 16 and rod 17 rearwardly to a position in which the ring 66 (previously adjusted to the required dosage) is at position O on the gauge 69. In such position, the gas in the chamber 11 is compressed and partially liquefied. At the same time, withdrawal or rearward movement of the piston rod 30 results in the drawing of injection fluid from the container 62 into the medicine chamber formed in the barrel 24 in front of the rod 30. In order to administer the medicine, the outer end of the plug 36 is placed against the skin, and the safety catch 92 is rotated 90° to connect the trigger 84 to the rod 112, releasing the ball 74 when the trigger is pressed. The piston is released, injection fluid is discharged from the barrel 24, and the charging liquid returns to the handle 70.

Advantage of the above described device include its small size, a relatively constant injection pressure, and simple construction. The use of quick disconnect joints between the barrel 24 and the plug 12, and between the piston rods 17 and 30 permit relatively rapid removal of parts for cleaning or replacement. The use of a ball-type clutch for stepwise pumping of charging liquid from the handle into the pressure chamber is relatively simple and efficient. The mounting of the medicine container 62 on the barrel makes it easy to use one device for injecting a variety of medicines. It is merely necessary to replace the barrel 24 and the rod 30 with another barrel and rod carrying a different medicine container.

Of course, the injector of the present invention can be used in other applications for discharging liquids other than medicines.

We claim:

1. A jet injector for administering a fluid medicine through the skin comprising:
   (a) an elongated tubular casing;
   (b) handle means substantially perpendicular to said casing;
   (c) plug means in said casing, said plug means dividing the interior of said casing into a medicine chamber and a compression chamber, said compression chamber containing a substance which is gaseous at normal room temperature and which converts to a liquid when subjected to pressure;
   (d) an inlet duct in said casing for introducing medicine into said medicine chamber;
   (e) a discharge orifice in said casing for discharging medicine from said medicine chamber into the skin;
   (f) first piston means slidably mounted in said compression chamber for movement from a rest position toward said substance to a charged position, and away from said substance to the rest position;
   (g) first rod means connected to said first piston means slidable in said plug means and extending into said medicine chamber for drawing medicine into and discharging medicine from said medicine chamber;
   (h) a charging chamber in said handle means containing a charging liquid;
   (i) a pressure chamber between said plug means and said piston means for receiving liquid from said charging chamber for pressing the first piston means against the substance;
   (j) second piston means in said handle means;
   (k) trigger means connected to said casing for moving said second piston means against said charging liquid, whereby said charging liquid is caused to pass from said charging chamber into said pressure chamber to move said first piston means against the substance to the charged position for liquefying a portion of said substance, and to cause said first rod means to move partially out of said medicine chamber for drawing medicine into the medicine chamber;
   (l) safety catch means in said handle means for locking said first and second piston means in the charged position, and for releasing said first and second piston means to cause said first rod means to force said medicine through said discharge orifice while the charging liquid is returned to the charging chamber.

2. A jet injector according to claim 1, wherein said casing includes a rear handle end portion on one side of said plug means carrying said handle means and defining said compression chamber, and barrel means on the other side of said plug means defining said medicine chamber.

3. A jet injector according to claim 2, wherein said barrel means is releasably connected to said plug means.

4. A jet injector according to claim 3, wherein said first rod means includes one piston rod connected to said first piston means and slidable in said plug means and a second piston rod releasable connected to said one piston rod and slidable in said barrel for drawing medicine into and discharging medicine from said medicine chamber.

5. A jet injector according to claim 1, including adjustable stop means on said first rod means for varying the stroke of said first rod means and consequently the dosage of medicine drawn into said medicine chamber.

6. A jet injector according to claim 1, wherein said trigger means is pivotally connected to said casing for gripping with said handle means.

7. A jet injector according to claim 6, including first valve means in said handle means between said charging chamber and said pressure chamber; bar means slidably mounted on said handle for movement by said trigger means; and sleeve means in said handle means connected to said second piston means for moving the second piston means against said charging liquid.

8. A jet injector according to claim 7, wherein said sleeve means is mounted on said safety catch means for movement in one direction with said bar means and second piston means to press the second piston means against the charging liquid and for free sliding movement in the reverse direction.

9. A jet injector according to claim 8, including spring means for returning said sleeve means in the reverse direction, whereby said trigger means can be pumped to cause reciprocating movement of said bar means and sleeve means.

* * * * *